(12) United States Patent
McDonald et al.

(10) Patent No.: US 9,993,329 B2
(45) Date of Patent: Jun. 12, 2018

(54) STENT AND STENT GRAFT PROSTHESIS

(75) Inventors: Gary Peter McDonald, Glasgow (GB); Vincent Nelis, Glasgow (GB)

(73) Assignee: VASCUTEK LIMITED, Renfrewshire, Strathclyde (GB)

( * ) Notice: Subject to any disclaimer, the term of this patent is extended or adjusted under 35 U.S.C. 154(b) by 0 days. days.

(21) Appl. No.: 14/123,667

(22) PCT Filed: Jun. 1, 2012

(86) PCT No.: PCT/GB2012/051234
§ 371 (c)(1),
(2), (4) Date: Jan. 8, 2014

(87) PCT Pub. No.: WO2012/164292
PCT Pub. Date: Dec. 6, 2012

(65) Prior Publication Data
US 2014/0121761 A1    May 1, 2014

(30) Foreign Application Priority Data
Jun. 3, 2011    (GB) .................................. 1109308.5

(51) Int. Cl.
  *A61F 2/06*    (2013.01)
  *A61F 2/07*    (2013.01)
  *A61F 2/89*    (2013.01)
(52) U.S. Cl.
  CPC .................. *A61F 2/07* (2013.01); *A61F 2/89* (2013.01); *A61F 2002/075* (2013.01); *A61F 2230/0095* (2013.01)

(58) Field of Classification Search
  CPC .... A61F 2/07; A61F 2/95; A61F 2/848; A61F 2/86; A61F 2/89; A61F 2002/075; A61F 2002/828; A61F 2002/8483; A61F 2002/8486
  See application file for complete search history.

(56) References Cited

U.S. PATENT DOCUMENTS

| | | |
|---|---|---|
| 4,580,568 A | 4/1986 | Gianturco |
| 5,405,378 A | 4/1995 | Strecker |
| 5,554,181 A | 9/1996 | Das |
| 5,720,776 A | 2/1998 | Chuter et al. |

(Continued)

FOREIGN PATENT DOCUMENTS

| | | |
|---|---|---|
| EP | 656198 A2 | 2/1991 |
| EP | 656198 A3 | 2/1991 |

(Continued)

OTHER PUBLICATIONS

Parodi et al., Annals of Vascular Surgery (1991) 5:491-499.
(Continued)

*Primary Examiner* — Melanie Tyson
(74) *Attorney, Agent, or Firm* — Heslin Rothenberg Farley & Mesiti P.C.

(57) ABSTRACT

A stent graft prosthesis includes spaced stent elements for location on a tubular graft. First and second stent elements are located in first and second locations on the graft. The second stent element includes a saddle shaped stent. The first stent element includes a ring shaped stent. Optionally a third stent element is also present. The tubular graft includes a graft sleeve. The prosthesis can be used for treatment of vascular disorders such as aortic aneurysm.

28 Claims, 5 Drawing Sheets

(56) References Cited

U.S. PATENT DOCUMENTS

Figure 1:
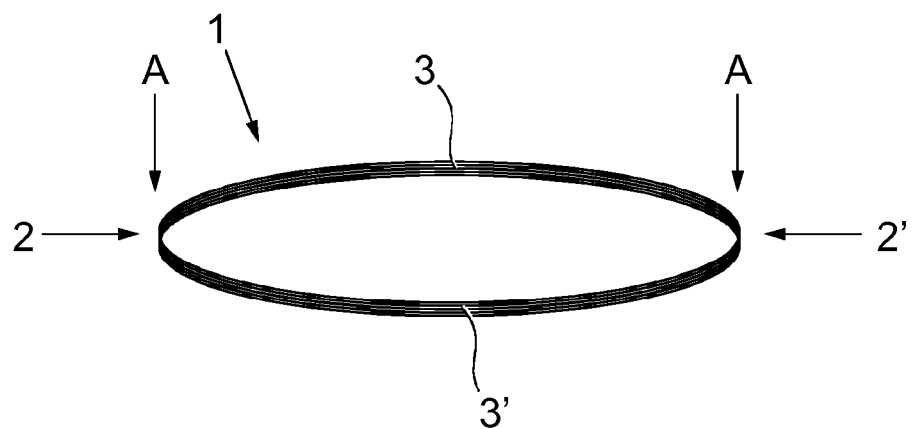

| | | | |
|---|---|---|---|
| 6,203,568 | B1 | 3/2001 | Lombardi et al. |
| 6,278,079 | B1 | 8/2001 | McIntyre et al. |
| 6,635,080 | B1 * | 10/2003 | Lauterjung et al. ......... 623/1.13 |
| 2004/0176833 | A1 * | 9/2004 | Pavcnik et al. .............. 623/1.13 |
| 2006/0184227 | A1 * | 8/2006 | Rust .......................... A61F 2/07 623/1.13 |
| 2008/0097570 | A1 * | 4/2008 | Thornton .................. A61F 2/07 623/1.11 |

FOREIGN PATENT DOCUMENTS

| | | |
|---|---|---|
| EP | 0686379 | 12/1995 |
| EP | 880979 A1 | 5/1998 |
| EP | 1796589 | 8/2010 |
| GB | 2470083 A | 5/2009 |
| WO | 9530385 A1 | 11/1995 |
| WO | 9737617 | 10/1997 |
| WO | 2006034340 | 3/2006 |
| WO | WO2010053563 | 5/2010 |
| WO | 2011056797 A1 | 5/2011 |
| WO | 2011117736 A2 | 9/2011 |

OTHER PUBLICATIONS

International Search Report dated Sep. 19, 2012 from PCT/GB2012/051234.

United Kingdom Intellectual Property Office Search Report dated Sep. 27, 2012 for GB1209759.8.

Office Action for European Application No. 12731617.2 dated Mar. 24, 2016.

* cited by examiner

STENT AND STENT GRAFT PROSTHESIS

RELATED APPLICATION

This application is a 371 of international application PCT/GB2012/051234, filed Jun. 1, 2012, and claims priority from GB application 1109308.5, filed Jun. 3, 2011, which is incorporated herein by reference in its entirety.

The present invention relates to a stent, and in particular to a stent which forms part of a stent graft prosthesis.

Artificial prostheses consisting of a tubular conduit having an open lumen are well-known and are used in medicine to replace diseased or damaged natural body lumens, such as, for example, blood vessels or other hollow organs for example bile ducts, sections of intestine or the like. The most common use of such artificial prostheses are to replace diseased or damaged blood vessels.

A number of vascular disorders can be treated by use of an artificial prosthesis. One relatively common vascular disorder is an aneurysm. Aneurysm occurs when a section of natural blood vessel wall, typically of the aortic artery, dilates and balloons outwardly. Whilst small aneurysms cause little or no symptoms, larger aneurysms pose significant danger to a patient. Rupture of an aortic aneurysm can occur without warning and is usually fatal, so significant emphasis is placed on early diagnosis and treatment. With an increasing ageing population, the incidence of aneurysm continues to rise in western societies.

Provided that an aneurysm is diagnosed prior to rupture, surgical treatment to repair the affected vessel wall is effective. Surgical treatment of aneurysm involves the replacement or reinforcement of the aneurismal section of aorta with a synthetic graft or prostheses under general anaesthesia allowing the patient's abdomen or thorax to be opened (see Parodi et al., Annals of Vascular Surgery (1991) 5:491-499). The patient will then have a normal life expectancy.

Surgical repair of aneurysm is however a major and invasive undertaking and there has been much effort in developing less invasive methods. Currently, aneurysm repair generally involves the delivery by catheter of a fabric or ePTFE graft which is retained at the required location by deployment of metallic stent elements. The ability to deliver the graft/stent device by catheter reduces the surgical intervention to a small cut-down to expose the femoral artery and, in suitable circumstances, the device can be deployed percutaneously. Catheter delivery is beneficial since the reduced invasive nature of the procedure allows utilisation of a local anaesthetic and leads to reduced mortality and morbidity, as well as decreased recovery time. For example, endovascular repair is typically used for repair of infra-renal abdominal aortic aneurysms where the graft is placed below the renal arteries. Many different types of devices useful for endovascular repair are now available, for example a resiliently engaging endovascular element described in U.S. Pat. No. 6,635,080 (Vascutek) or a tubular fabric liner having a radially expandable supporting frame and a radiopaque marker element stitched to the liner as disclosed in U.S. Pat. No. 6,203,568 (Medtronic).

However, whilst the endovascular repair of aneurysms is now accepted as the method of choice, the technique has significant limitations and is not suitable for all patients.

As mentioned above, other vascular disorders are treatable by use of a vascular prosthesis. Examples include (but not limited to) occlusions, stenosis, vascular damage due to accident or trauma, and the like. Vascular prostheses are also used in by-pass techniques.

Endovascular techniques involve the delivery of a prostheses by catheter. Since the internal lumen of the catheter defines the maximum dimensions of the prostheses to be inserted, much effort has been expended in the design of prostheses which can be packaged in a minimal volume, and are easy to deploy once positioned at the required location.

One successful type of prosthesis, is a stent graft comprising a conduit formed from a flexible sleeve attached to a rigid support or stent. The sleeve will typically be made of a fabric (usually a knitted or woven fabric) of ePTFE, PTFE or polyester (for example DACRON) polyethylene or polypropylene and may optionally be coated to reduce friction; discourage clotting or to deliver a pharmaceutical agent. The fabric will generally be porous on at least one surface to enable cell in growth. The stent may be balloon-expandable (eg. a PALMAZ stent made of rigid stainless steel wire), but could also be self-expandable and formed of a shape memory material, such as nitinol (a nickel-titanium alloy). Numerous different stent designs are known in the art, for example braided stents as described in EP 880979 or wire zig-zag stents as described in U.S. Pat. No. 4,580,568.

Stent grafts are commonly formed with a plurality of stents spaced along the graft. Even spacing of the stents ensures that the crush strength of the graft does not vary along its length. However, whilst the spacing between the stents allows the graft to be curved when inserted in a body vessel, the degree of curvature is limited by the stent spacing. WO 2010/053563 describes a stent graft designed for deployment in a curved vessel. Identical stents are spaced further apart from each other in the region of the stent graft which undergoes the greatest curvature. Thus, the inter-stent spacing varies along at least part of length of the graft. However, for treatment of aneurysm, it is desirable that the stent graft exhibits a degree of stiffness across the diseased (aneurismitic) portion of the blood vessel under repair.

Moreover, stent grafts having such ring stent elements have the disadvantage that the rings lack stability, and in particular the rings have a tendency to rotate or tilt relative to each other either during deployment or following deployment.

There is a need for a stent graft prosthesis having the ability to adopt a high degree of curvature at one location along its length whilst maintaining the ability to seal well at both ends. Desirably the stent graft prosthesis will also have a relatively stiff portion able to extend along an aneurysm and which is suitable for engagement with a secondary graft.

The present invention seeks to provide an improved stent arrangement in a stent graft.

According to one aspect the present invention provides a stent member comprising a plurality of spaced stent elements for location on a tubular graft, wherein a first stent element is located in a first location on said graft, and wherein a second stent element is located in a second location or said graft, and wherein the second stent element comprises a saddle shaped stent. Generally, the first location is at or close to one end of the graft to which the first stent member is attached. Generally, the second location is located in the central region of the graft. The stent member of the present invention can be used to form a stent graft prosthesis.

Each stent element can independently be formed of one or more stents.

The tubular graft is also referenced herein as a "graft sleeve".

The first stent element can comprise at least one stent which is ring-shaped (annular) and has an inner circumference substantially identical to (preferably identical to) the outer circumference of the graft sleeve (the tubular graft). By "substantially identical to" we refer to a circumference which is equal to or up to 5% greater than the outer circumference of the graft sleeve, preferably which is equal to or up to 2% greater than the outer circumference of the graft sleeve and more preferably equal to or up to 1% greater than the outer circumference of the graft sleeve.

The second stent element can comprise a stent which is sinusoidal, i.e. saddle shaped. By "saddle shaped" we refer to a circular ring stent formed of a material which is sufficiently resilient to be distorted so that a first pair of diametrically opposed points on the circumference of the ring are displaced in one axial direction whilst a second pair of diametrically opposed points, centrally located on the circumference between the first pair, are displaced in the opposing axial direction to form a symmetrical saddle shape. For convenience, the first pair of points can be described as "peaks", with the second pair of points described as "valleys". The degree of axial displacement between the first pair of points and the second pair of points (which axial displacement is also termed the "saddle height"), is a function of the original circumference of the ring stent prior to its distortion, relative to the final circumference of a circle within which the distorted (saddle shaped) configuration can be located. Thus, the ratio of final circumference:original circumference provides a simplistic notation of the axial displacement. Generally the final circumference will be the outer circumference of the graft sleeve to which the stent is to be attached. The percentage oversize of the undistorted inner circumference of the circular stent relative to the outer circumference of the graft sleeve also gives a convenient measure of the saddle shape adopted, and can be calculated as:

$$\text{Oversize \%} = \frac{[\text{Stent inner diameter} - \text{Graft sleeve outer diameter}]}{\text{Graft sleeve outer diameter}} \times 100\%$$

Optionally, the stent member also comprises a third stent element having at least one stent with a saddle shape different to that of each stent in the second stent element. Desirably the third stent element comprises a stent which has a saddle shape with a greater degree of axial displacement relative to the saddle shape of at least one stent of the second stent element.

Thus, the saddle height of at least one stent in the third stent element is higher than that of at least one stent in the second stent element.

Optionally the first stent element can comprise two stents: a saddle-shaped stent and a ring stent. Thus, the first stent element comprises a terminal stent formed of a continuous loop of resilient material (nitinol or PEEK or the like) having a sinusoidal (saddle) shape as described above. This saddle shaped stent can have a saddle height of 4 to 8 mm and is conveniently located at one end of the graft sleeve. A second stent formed in a continuous loop and in circular form with an inner circumference substantially identical to the outer circumference of the graft sleeve is also present as part of the first stent element. The second stent can also be formed from resilient material (nitinol or PEEK or the like). The resilient material can be formed as an elongate strand and wound into a loop as required for the terminal stent and/or the second stent. Conveniently these two stents are spaced 5 to 13 mm apart (for example 5 to 8 mm at the closest point) and provide good sealing of the graft prosthesis against the luminal wall of the blood vessel.

The second stent element can comprise 2, 3, 4 or 5 separate saddle shaped stents. Optionally the size of the valleys and peaks in the saddle shape can increase monotonically between the stents forming the second stent element. Optionally the second stent element comprises saddle shaped stents with two different saddle heights. Thus, the second stent element comprises two distinct saddle shape stent types, differentiated by their saddle height. For example one saddle shaped stent in the second stent element can have a saddle height of 4 to 8 mm, and a further saddle shaped stent can have a saddle height of 8 to 15 mm. The stents can be placed 12 to 25 mm apart. One or more stents of each saddle shape can be present in the second stent element. Conveniently stents with a lower saddle height neighbour the first stent element.

The third stent element can comprise 2, 3, 4, 5, 6, 7, 8, 9 or 10 separate saddle shaped stents. A suitable saddle height for each stent in the third stent element can be independently selected from a range of 10 to 25 mm, for example 13 to 22 mm. Optionally the size of the valleys and peaks in the saddle shape can increase monotonically between the stents forming the third stent element. Thus, the axial displacement can increase step wise along the length of the prosthesis. Alternatively the saddle height selected can be the same for all stents in the third stent element. The stents can be spaced 12 to 30 mm apart.

Conveniently the spacing of each stent in the third stent element is such that the peak of one stent is traversely aligned with the valley of its immediate neighbour. Optionally, the peaks and valleys of each stent element is longitudinally aligned with the peaks and valleys, respectively, of its immediate neighbour. This arrangement provides increased axial and tensional stiffness.

Each of the individual stents in the first stent element, second stent element, or third stent element, can independently be conveniently formed from multiple windings of a wire. Nitinol wire is suitable. The number of strands of wire can be varied according to the diameter of wire utilised and the size of graft. The number of strands wound can vary from 2 to 120 or even more, but would typically have 10 to 30 strands forming the ring stent. Any diameter wire which maintains the required resilience can be used. Suitable diameters for the wire can be selected from a range of 0.1 mm to 2 mm, for example 0.5 mm to 1 mm.

Each stent can be independently formed of any suitable biocompatible material having the necessary resilience to fold inwardly into a first folded configuration (ie. for packaging) and to adapt a second open configuration (ie. after deployment). Mention can be made of shape memory materials such as, for example, nitinol. Resilient polymers are also suitable, particularly engineering high modulus polymers such as polyether ether ketone (PEEK). PEEK polymer with shape memory behaviour can be used.

In a second aspect, the present invention provides a stent graft prosthesis, said prosthesis having a tubular graft, a first stent element attached to the tubular graft, a second stent element attached the tubular graft, and a third stent element attached the tubular graft, wherein:

the first stent element comprises a stent which is a substantially circular ring stent;

the second stent element comprises at least one ring stent which has an oversize of 2 to 25% and which is arranged in a saddle shape; and the third stent element comprises at least one ring stent which has an oversize of 20 to 30% and which is arranged in a saddle shape.

Optionally, the second stent element comprises at least two ring stents each having the stated oversize. Desirably these ring stents are attached such that the peaks and valleys forming the saddle shape are longitudinally aligned along the longitudinal axis of the graft. In one embodiment, the second stent element has three, four or five ring stents having the stated oversize, and each ring stent is attached so that the peaks and valleys are longitudinally aligned with each other along the longitudinal axis of the graft. Together the ring stents forming the second stent element provide a zone of relative flexibility, allowing an increased degree of curvature to be accommodated.

Optionally, the third stent element comprises at least 4 ring stents each having the stated oversize. Desirably these ring stents are attached such that the peaks and valleys forming the saddle shape are longitudinally aligned along the longitudinal axis of the graft. In one embodiment, the third stent element has 5, 6, 7, 8, 9 or 10 ring stents having the stated oversize, and each ring stent is attached so that the peaks and valleys are longitudinally aligned with each other along the longitudinal axis of the graft. Together the ring stents forming the third stent element provide a zone of relative axial and torsional stiffness. Optionally, the peak of one ring stent is traversely aligned with the valley of its immediate neighbour.

Optionally, the peaks and valleys of the stents forming the second stent element and the peaks and valleys of the stents forming the third stent element are also aligned longitudinally.

The stent graft prosthesis can also comprise a fourth stent element. The fourth stent element comprises a ring stent which is preferably substantially circular and has an inner circumference substantially identical to the outer circumference of the graft sleeve at the location where it is attached. Optionally, the fourth stent element comprises a saddle shaped ring stent which is the penultimate stent on one end of the graft sleeve and also a circular ring stent as described above which forms the terminal stent at that end. The combination of these two stents, provides the necessary degree of rigidity and sealing required at the terminal end of the prosthesis. In particular we have found that an arrangement where the valley of the saddle shaped penultimate stent is located in close proximity (ie. immediately adjacent to or touching the circular ring stent or within 1 to 2 mm of it) to the circular ring stent significantly improves the sealing effect.

The graft sleeve can be flexible and is usually formed of a woven or knitted fabric. The sleeve will usually be substantially impervious to fluid.

Optionally, at least one surface of the graft sleeve will be sufficiently porous to facilitate cell ingrowth. Suitable materials include polyester, polyethylene, propylene, ePTFE, PTFE and the like. The sleeve can be coated to reduce impermeability or to delivery a biological agent.

For many intended uses, the sleeve can conveniently be formed with a constant diameter. However tapered grafts (ie. where the diameter varies along its length) are also possible and are particularly useful for certain indications.

The stent graft prosthesis can be inserted into the patient using a delivery catheter and, once correctly located at the site requiring treatment, is deployed by the withdrawal of a delivery sheath of the delivery catheter. Balloon-expandable grafts are then caused to expand in diameter by inflation of a balloon located within the lumen of the graft. Self-expandable grafts radially expand upon release from the outer tube. Irrespective of the mode of expansion, once deployed, the stents hold the graft in location by contact with the inner walls of the blood vessel.

Since the stent graft prosthesis will need to be compressed for loading into the catheter and during delivery, in general terms, each stent is formed from the minimum amount of material able to maintain the patency of the sleeve lumen at the required diameter.

Each stent can conveniently be positioned externally of the sleeve of the stent graft.

Conveniently, each stent is attached to the graft sleeve by sewing, but any other suitable means of attachment to the sleeve (eg. adhesive or heat bonding) could alternatively be used.

In one aspect, the present invention provides a stent graft prosthesis comprising:
i) a sleeve having a first end and a second end with a lumen extending therethrough;
ii) first, second and third stent elements attached to the sleeve a pre-selected distance apart;
wherein the first stent element comprises at least one ring stent having an inner circumference substantially identical to the outer circumference of the sleeve, wherein the second stent element comprises at least 2 saddle shaped stents wherein the saddle height is at least 5 mm, and wherein the third stent element comprises at least two saddle shaped stents wherein the saddle height is at least 10 mm.

The graft sleeve can be flexible and is usually formed of a woven or knitted fabric. The sleeve will usually be substantially impervious to fluid.

Optionally, at least one surface of the graft sleeve will be sufficiently porous to facilitate cell ingrowth. Suitable materials include polyester, polyethylene, propylene, ePTFE, PTFE and the like. The sleeve can be coated to reduce impermeability or to delivery a biological agent.

For many intended uses, the sleeve can conveniently be formed with a constant diameter. However tapered grafts (ie. where the diameter varies along its length) are also possible and are particularly useful for certain indications.

The pre-selected distance between each stent can conveniently be such that the peak of one saddle shaped stent is traversely aligned (relative to the longitudinal axis of the graft sleeve) with the valley of an adjacent saddle shaped stent. Thus, having regard to FIG. 2, the stents will be placed a distance D apart, wherein D corresponds to the saddle height.

The stents can each be formed from nitinol wire and will typically include multiple windings of nitinol wire. Each stent can be attached to the external surface of the sleeve or to the internal (luminal) surface of the sleeve. Generally, it is more convenient to attach the stents to the external (non-luminal) surface of the sleeve.

In an embodiment of the stent graft of the present invention, the first stent element is located at or close to the first or second end of the sleeve. For example, although distances will vary with dimensions of the stent graft, the first stent element can conveniently be located from 0 to 2 cm from either the first or second end of the sleeve.

A suitable pre-selected distance between two stents of the second stent element is from 0.5 to 5 cm, preferably 0.5 to 3 cm. One of skill in the art will however be aware that the pre-selected distance between the stents will depend upon factors such as the size (diameter and/or length) of the stent graft, its intended location in the patient, the patient's anatomy and medical condition.

A suitable pre-selected distance between two stents of the third stent element is from 0.5 to cm, preferably 0.5 to 3 cm. One of skill in the art will however be aware that the pre-selected distance between the stents will depend upon factors such as the size (diameter and/or length) of the stent graft, its intended location in the patient, the patient's anatomy and medical condition.

In a further aspect, the present invention provides an implantable prosthesis comprising:
i) a compliant and substantially fluid impervious tubular sleeve having a proximal end and a distal end with a conduit therethrough;
ii) a first stent element comprising at least one stent formed from multiple windings of wire of a shape memory material, attached to said sleeve at a first location thereon;
iii) a second stent element attached to said sleeve comprising at least two stents, each formed from multiple windings of wire of a shape memory material, each stent having a saddle shape configuration with two diametrically opposed peaks and two diametrically opposed valleys, the valleys being axially displaced relative to the peaks, wherein the peaks of each stent are aligned longitudinally; and
iv) a third stent element attached to said sleeve comprising at least two stents, each formed from multiple windings of wire of a shape memory material, each stent having a saddle shape configuration with two diametrically opposed peaks and two diametrically opposed valleys, the valleys being axially displaced relative to the peaks, wherein the peaks of each stent are aligned longitudinally, wherein each peak of each stent in the second stent element is longitudinally aligned with a peak of each stent in the third stent element, and wherein the axial displacement between the peaks and valleys of each stent in the third stent element is larger than the axial displacement between the peaks and valleys of each stent in the second stent element.

In a further aspect, the present invention provides a method of treating an aneurysm of the aortic arch, said method comprising inserting a stent graft prosthesis as described in any of the embodiments set out above such that the first stent element sealingly engages with the inner luminal wall of the aorta, the second stent element provides the flexibility able to accommodate the angulation associated with the descending thoracic arch, and the third stent element provides axial and torsional stiffness required to ensure the integrity of the graft within the aneurysm sac and/or within the longer straighter section of the descending aorta. Optionally, as indicated above, the stent graft prosthesis can also include a fourth stent element which includes a ring stent having an inner circumference substantially identical to the outer circumference of the graft sleeve. This fourth stent element operates in a similar manner to the first stent element and sealingly engages at the distal end of the stent graft in order to totally exclude the affected area of the diseased aorta. The fourth stent element can also provide an effective docking zone for any secondary stent grafts which may be required.

In one embodiment, the fourth stent element in addition to a circular ring stent also includes two U-shaped stent portions which are located diametrically opposite each other and which are located substantially parallel to the valleys of the neighbouring stent in the third stent element.

In a further aspect, the present invention provides a method of treating a patient in need thereof, said method comprising implanting a prosthesis comprising a tubular graft, a first stent element attached to the tubular graft, a second stent element attached to the tubular graft and a third stent element attached to the tubular graft, wherein the first stent element comprises a substantially circular ring stent, the second stent element comprises at least one stent formed as a continuous loop and attached to the tubular graft in a saddle shape; and the third stent element comprises at least one stent formed as a continuous loop and attached to the tubular graft in a saddle shape.

In a further aspect, the present invention provides a method of manufacturing a prosthesis suitable for implantation into the body, said method comprising;
(i) providing a flexible tubular conduit;
(ii) providing a first stent element comprising a stent in the form of a continuous loop and attaching said stent to the conduit, so the stent describes a circumference of the tubular conduit;
(iii) providing a second stent element comprising a stent in the form of a continuous loop and attaching said stent to said tubular conduit so that the stent describes a first saddle shape having peaks and valleys;
(iv) providing a third stent element comprising a stent in the form of a continuous loop and attaching said stent to the tubular conduit such that the stent describes a second saddle shape having peaks and valleys aligned with the respective peaks and valley of the stent of the second stent element.

Preferred or alternative features of each aspect or embodiment of the invention apply mutatis mutandis to each other aspect or embodiment of the invention, unless the context demands otherwise.

Figure 2:
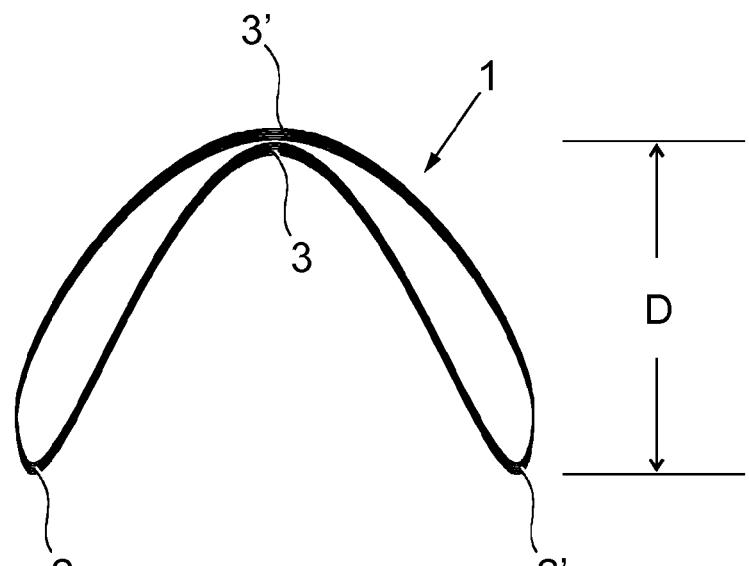
Figure 3:
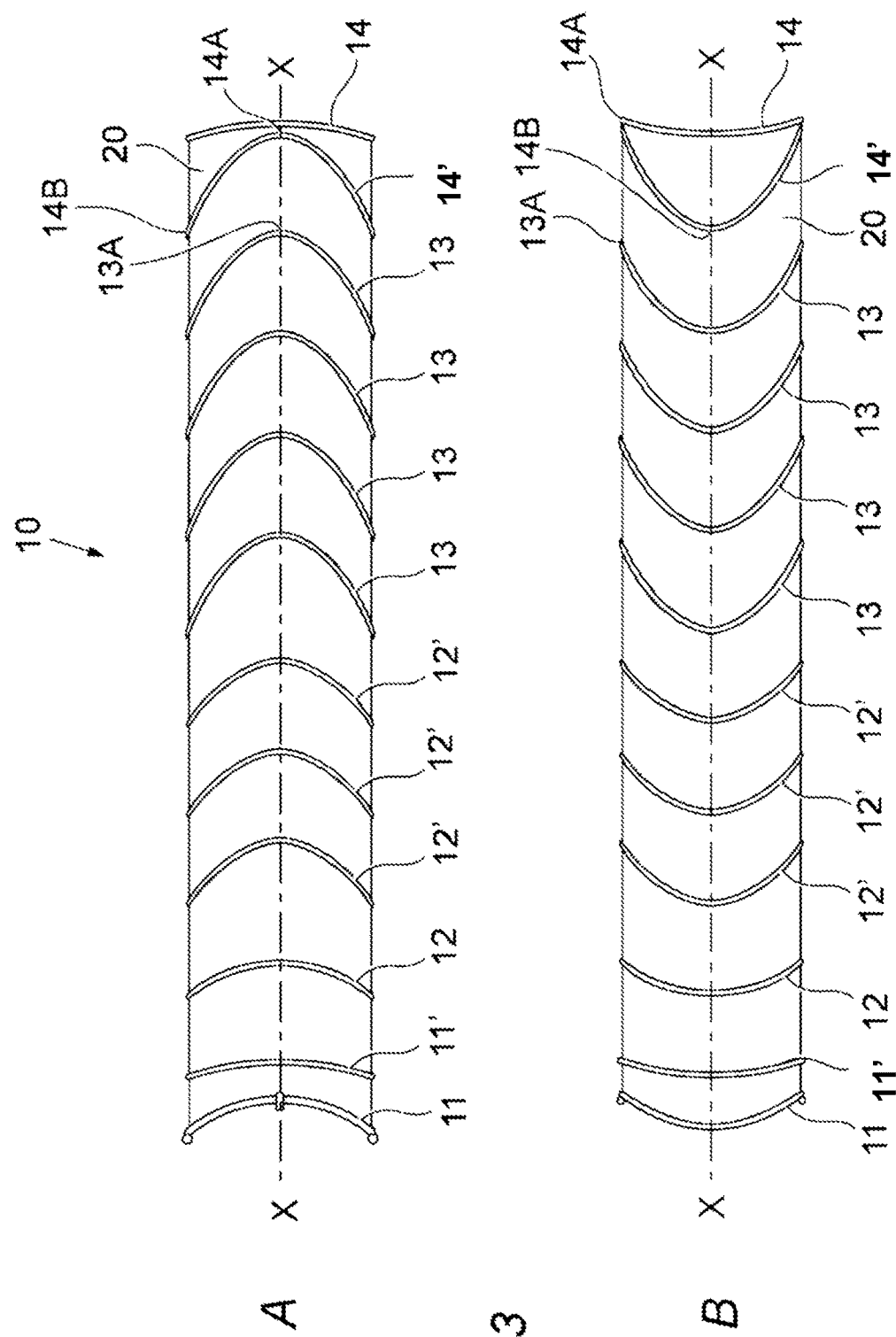
Figure 4:
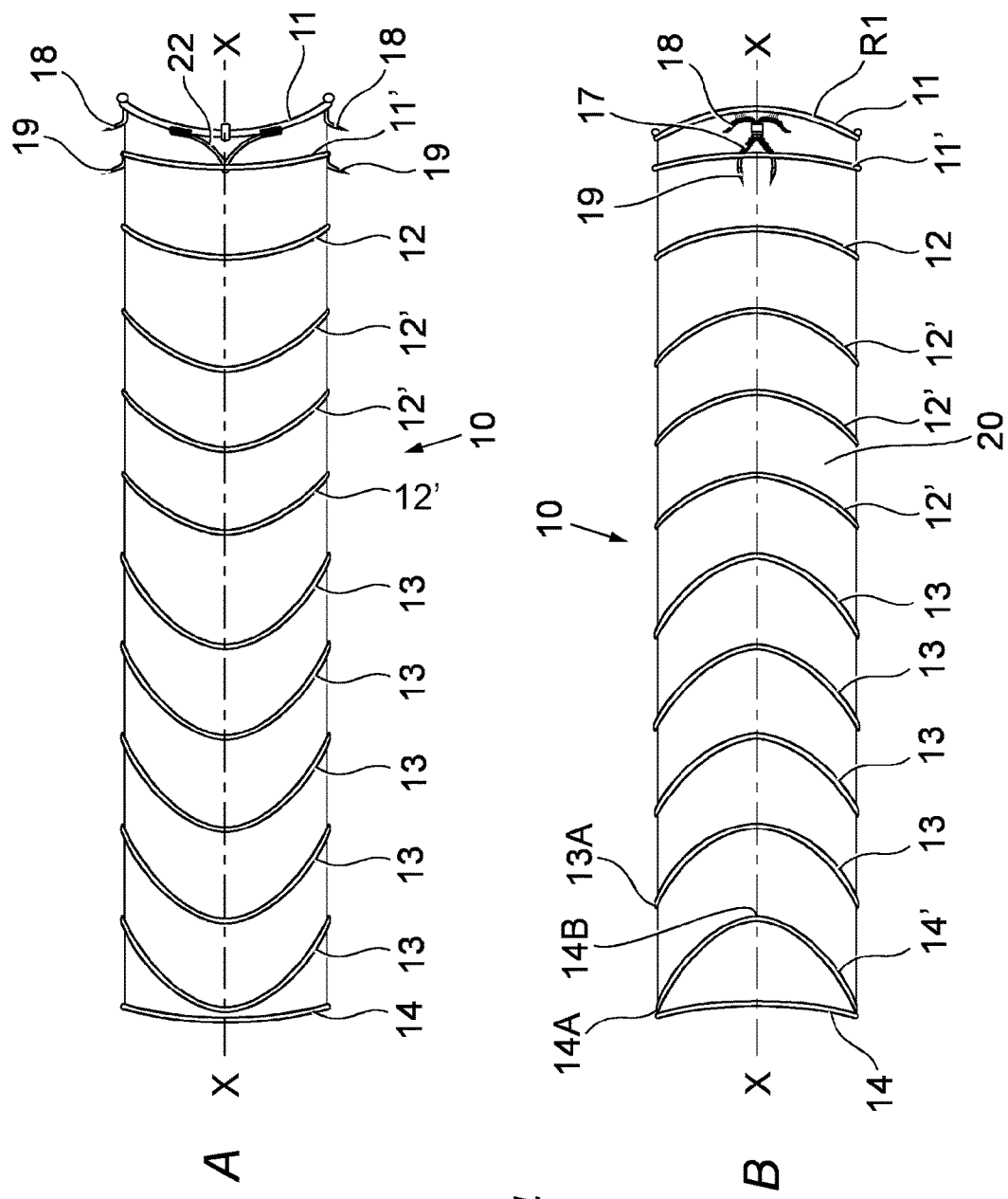
Figure 5:
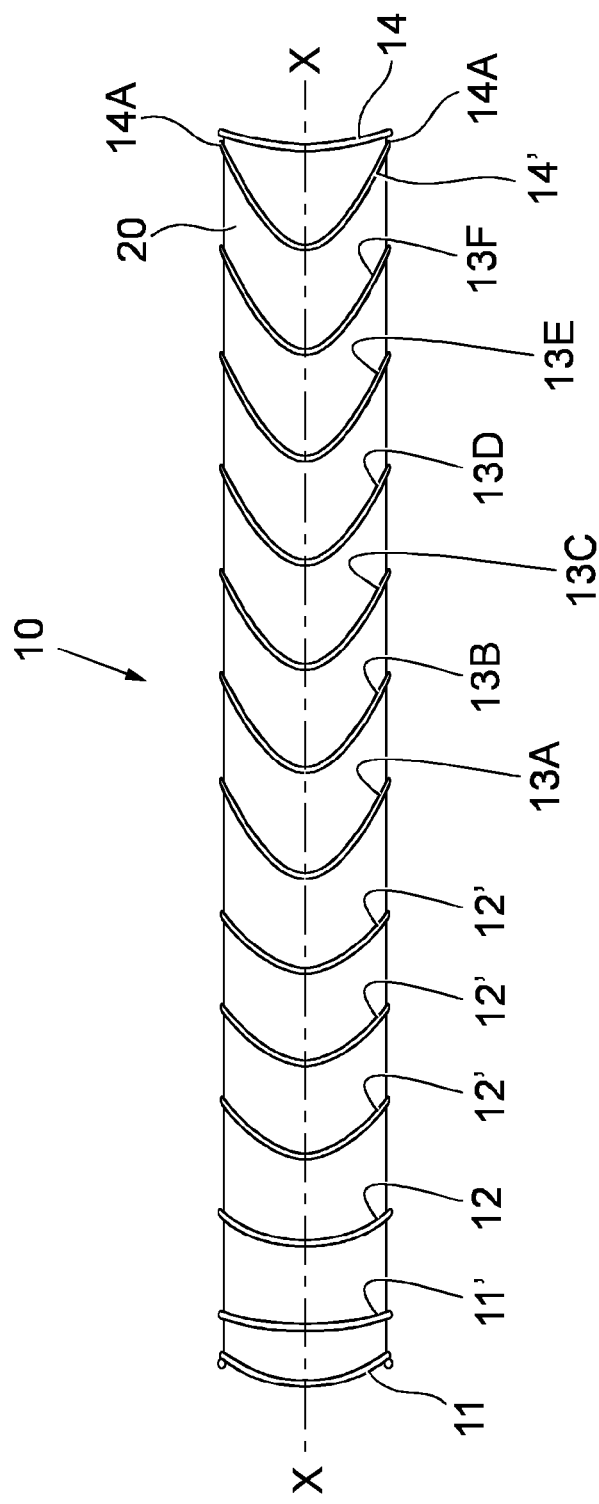
Figure 6:
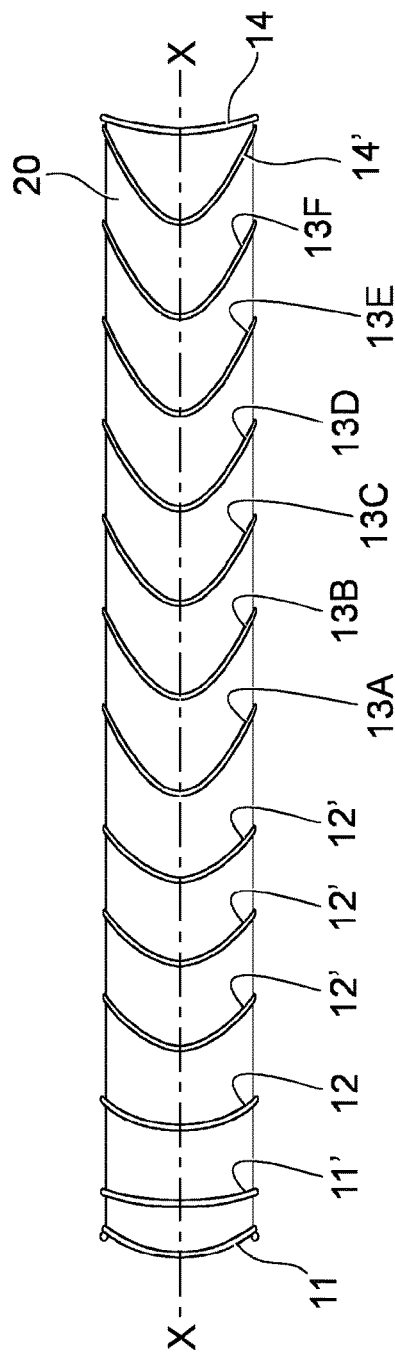
Figure 6:
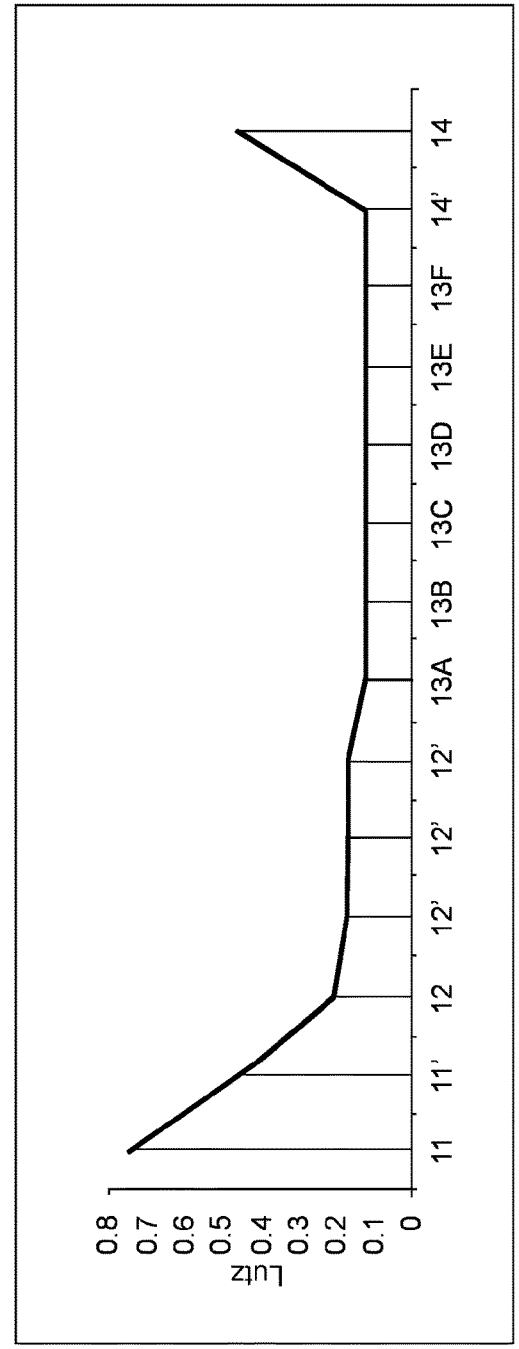

The present invention will now be further described by reference to the following figures, in which:

FIG. 1: is a schematic illustration of a stent in the form of a continuous loop suitable for use in the present invention;

FIG. 2: is a schematic illustration of the stent of FIG. 1 distorted into a saddle shape;

FIG. 3: is a schematic illustration of a stent graft of the present invention showing: A the front view; and B the side view of the graft;

FIG. 4: is a schematic illustration of a stent graft of the present invention showing: A the front view; and B the side view of the graft;

FIG. 5: is a schematic illustration of a further embodiment of the stent graft of the present invention; and FIG. 6: shows the graft of FIG. 5 with the profile of stent strength factor according to zone function.

Referring to the drawings, FIG. 1 shows a stent 1 suitable for use in the invention formed from multiple windings of nitinol wire. As illustrated, the stent 1 is in the form of a continuous loop in a substantially circular configuration, and in that configuration is suitable for use as a stent in the first or fourth stent elements in the stent graft of the present invention. Four equidistant points are indicated around the circumference of stent 1. Points 2,2' are diametrically opposed to each other and points 3,3' are diametrically opposed to each other. Points 3,3' are centrally located between point 2,2', and vice versa. Where the inner circumference of ring stent 1 is larger than the outer circumference of the graft or sleeve of the prosthesis, ring stent 1 can be distorted by displacing points 2,2' in the direction of arrows A to form the saddle shape configuration illustrated in FIG. 2. As illustrated, points 2,2' each form a "valley" of the saddle shaped stent and points 3,3' each form a "peak". Of course, the orientation of the saddle shape stent could be reversed with points 3,3' being displaced in the direction of arrows A thus forming the valleys with points 2,2' forming the peaks. The "saddle height" is defined as the longitudinal displacement between a peak and a valley as illustrated in FIG. 2 by distance D.

FIG. 3 shows a stent graft prosthesis 10 according to the present invention. The front view is shown in FIG. 3A and the side view is shown in FIG. 3B. As illustrated, the stent graft 10 comprises a tubular sleeve 20 formed from a substantially fluid impervious material such as woven polyester. Other suitable fabrics could alternatively be used. First, second, third and fourth stent elements are attached onto the outer surface of sleeve 20, for example by sewing using a suture material. The first stent element is formed from two ring stents 11, 11'. Each ring stent 11, 11' is formed from multiple windings of a resilient material such as PEEK or nitinol wire. As illustrated, the first stent element comprises a terminal stent 11 having a shallow saddle shape (ie. has an oversize of 3 to 4% relative to the outer circumference of the graft sleeve giving a saddle height of 4 to 8 mm) and which is located at one terminus of graft sleeve 20. Ring stent 11' is located a spaced distance, for example 5 to 13 mm, from stent 11 and has an inner diameter which is equal to or not more than 1% greater than the outer diameter of graft sleeve 20. Together stents 11 and 11' form a good sealing zone at the end of the prosthesis.

The second stent element, as illustrated, is formed from four separate stents 12, 12' each formed from a continuous loop of multiple windings of PEEK or of nitinol wire, distorted into a saddle shape with the peaks/valleys longitudinally aligned in the direction of longitudinal axis X. As illustrated, the second stent element has stents in two distinct saddle shaped forms; stent 12 has a relatively small saddle height relative to the other three stents 12' which have a larger saddle height. An exemplary saddle height for stent 12 is 4 to 8 mm. An exemplary saddle height for each stent 12' is 8 to 15 mm. The saddle height of each stent 12' can be the same or different.

As illustrated, the third stent element comprises three separate stents 13, each formed from a continuous loop of multiple windings of PEEK or nitinol wire, distorted into a saddle shape configuration. An exemplary saddle height for stent 13 is 13 to 22 mm. The saddle height of each of stent 13 can be constant (as illustrated) or could increase with distance away from the second stent element.

The embodiment illustrated includes a fourth stent element formed of two stents; a saddle shaped stent 14' and a circular stent 14 which are each formed from a ring stent of nitinol wire or of PEEK. Stent 14 has an inner circumference substantially identical to the outer diameter of graft sleeve 20 or which is up to 1% greater than the outer diameter of graft sleeve 20. An exemplary saddle height for stent 14' is 13 to 22 mm. As best seen in FIG. 3A the valley 14A of stent 14' is located close to, ie. within 2 mm of, stent 14. This arrangement provides a good sealing zone at this end of graft 10.

Having regard to FIGS. 3A and 3B, stents 13,14' are attached so that the peak of each stent 13,14' is traversely aligned with the valley of the immediately neighbouring stent. Thus, the peak 14B of stent 14' shown in FIG. 3A is aligned with the valley 13A of the neighbouring stent 13 (see also FIG. 3B). This arrangement increases the axial and torsional stiffness of the portion of the prosthesis covered by the third and fourth stent elements.

FIG. 4 shows an alternative stent graft prosthesis 10 according to the present invention. The front view is shown in FIG. 4A and the side view is shown in FIG. 4B. As illustrated, the stent graft 10 comprises a tubular sleeve 20 formed from a flexible fabric such as knitted or woven polyester. The sleeve should be biocompatible and substantially impervious to blood. Alternative fabric materials could also be used. Optionally, the sleeve could be coated internally or externally prior to attachment of the stent elements. The coating may deliver a biologically active ingredient or may decrease the permeability of the fabric. Although the sleeve is shown with a constant diameter, the sleeve could also be formed with a taper, ie. to have a varying diameter.

The stent elements are shown attached to the external surface of the fabric sleeve. Generally this is convenient for manufacture, but it is also possible for some or all of the stent elements to be attached internally, within the lumen of sleeve 20.

The first stent element is formed from two substantially circular ring stents 11,11'. Ring stents 11,11' are each formed from multiple windings of a resilient material such as PEEK or nitinol wire. Ring stent 11 is attached to the first end of sleeve 20. The distance between ring stents 11 and 11' is approximately 5 to 13 mm (preferably 6 to 9 mm at the closest location). For example, for a device having a sleeve outer diameter of 26.0 mm, the spacing between the stents 11 and 11' can be 6.5 mm at the closest location and 8.8 mm at the widest location. Stent 11' has a shallow saddle shape, for example the inner diameter of stent 11' can have a % oversize of 3 to 4% relative to the outer diameter of graft sleeve 20 at that location The second stent element, as illustrated, is formed from four separate stents 12, 12' each formed from continuous multiple windings of PEEK or nitinol wire, distorted into a saddle shape with the peaks/valleys longitudinally aligned in the direction of longitudinal axis X. As illustrated, the second stent element has two distinct saddle shaped forms, stent 12 and stent 12'. Stent 12 has a relatively small saddle height, typically in the range of 4 mm to 8 mm, whereas each stent 12' has a greater saddle height, typically in the region of 9 mm to 14 mm. In the embodiment illustrated, there are three stents 12', but this number may vary with the diameter and length of sleeve 20. For example, a single copy of stent 12' would be sufficient for a graft of length 120 mm, whereas two copies of stent 12' may be desired in a graft of length 170 mm. Similarly, three or four copies of stent 12' could be used in a longer graft, for example 220 mm. The saddle height of each stent 12' can be the same or different.

FIG. 4 also shows a third stent element comprising four separate stents 13, each formed from a continuous loop of multiple windings of PEEK or nitinol wire, distorted into a saddle shaped configuration. Typically, the saddle shape configuration of stent 13 has a saddle height of from 14 mm to 22 mm. In the embodiment illustrated, four separate third stents 13 are shown, but one of skill in the art would understand that this number may vary depending upon the final length of the graft required. For example, 3, 4, or 5 copies of third stent 13 may be present in a graft having a length of up to 120 mm. Generally, fewer copies of the third stent 13 will be required with increased diameter of the graft sleeve. Similarly, 4, 5, 6, 7 or 8 copies of stent 13 could be present in a longer graft, for example of length 170 mm. Likewise, 6, 7, 8 or 9 copies of stent 13 could be present in a longer graft, for example of length 220 mm. The saddle height of each stent 13 can be the same or different.

The stent graft prosthesis 10 illustrated in FIG. 4 also includes a fourth stent element 14 which is formed from a ring stent 14 and a saddle shaped stent 14'. Stent 14 has an inner circumference substantially identical to the outer circumference of graft sleeve 20. Optionally, a slight oversize of ring stent 14 can be selected to induce a small saddle shape, for example having a saddle height of 2.0 to 3.0 mm. Saddle shaped stent 14' has a saddle height of 14 to 22 mm and is positioned so that its valley 14A is located close to (ie. up to 2 mm) or touching ring stent 14 (see FIG. 4B).

Having regard to FIGS. 3A and 3B, stents 13, 14' are attached so that the peak of each stent 13,14' is traversely aligned with the valley of the immediately neighbouring stent. Thus, the peak 14B of stent 14' shown in FIG. 4A is aligned with the valley 13B of the neighbouring stent 13 (as shown in FIG. 4B). This arrangement increases the axial and torsional stiffness of the portion of the prosthesis to which the third and fourth stent elements are attached.

Tables 1 and 2 below illustrates possible stent size and spacing suitable for the stent graft prosthesis of FIG. 4.

TABLE 1

Device Ring Configuration per Diameter permutation.

| | | Sleeve Outer Diameter (mm) | | | | | | |
|---|---|---|---|---|---|---|---|---|
| | | 26.0 | 28.0 | 30.0 | 32.0 | 34.0 | 36.0 | 38.0 |
| | | | | | Graft No. | | | |
| | | T28 | T30 | T32 | T34 | T36 | T38 | T40 |
| | | | | Saddle Heights (mm) | | | | |
| Stent | 11 | 4.6 | 5.0 | 5.5 | 5.9 | 6.3 | 6.7 | 7.2 |
| | 11' | 2.3 | 2.4 | 2.5 | 2.6 | 2.7 | 2.8 | 2.9 |
| | 12 | 4.6 | 5.0 | 5.5 | 5.9 | 6.3 | 6.7 | 7.2 |
| | 12' | 9.5 | 10.2 | 10.9 | 11.6 | 12.3 | 13.0 | 13.6 |
| | 13, 14' | 14.8 | 15.8 | 16.8 | 17.9 | 18.9 | 20.0 | 21.0 |
| | 14 | 2.3 | 2.4 | 2.5 | 2.6 | 2.7 | 2.8 | 2.9 |
| | | | | Ring Spacing (mm) | | | | |
| Valley Spacing | 11-11' | 6.5 | 6.6 | 6.7 | 6.8 | 6.9 | 7.0 | 7.1 |
| | 11'-12 | 13.3 | 14.6 | 15.9 | 17.3 | 18.6 | 19.9 | 21.3 |
| | 12-12' | 18.6 | 19.7 | 20.7 | 21.9 | 23.0 | 24.1 | 25.0 |
| | 12'-12' | 13.6 | 14.5 | 15.4 | 16.2 | 17.1 | 18.0 | 18.8 |
| | 12'-13 | 18.9 | 20.1 | 21.3 | 22.5 | 23.7 | 25.0 | 26.2 |
| | 13-13 | 14.8 | 15.8 | 16.8 | 17.9 | 18.9 | 20.0 | 21.0 |
| | 13-14' | 14.8 | 15.8 | 16.8 | 17.9 | 18.9 | 20.0 | 21.0 |
| | 14'-14 | 2.0 | 2.0 | 2.0 | 2.0 | 2.0 | 2.0 | 2.0 |
| Peak Spacing | 11-11' | 8.8 | 9.2 | 9.7 | 10.1 | 10.5 | 10.9 | 11.4 |
| | 11'-12 | 11.0 | 12.0 | 12.9 | 14.0 | 15.0 | 16.0 | 17.0 |
| | 12-12' | 13.7 | 14.5 | 15.3 | 16.2 | 17.0 | 17.8 | 18.6 |
| | 12'-12' | 13.6 | 14.5 | 15.4 | 16.2 | 17.1 | 18.0 | 18.8 |
| | 12'-13 | 13.6 | 14.5 | 15.4 | 16.2 | 17.1 | 18.0 | 18.8 |
| | 13-13 | 14.8 | 15.8 | 16.8 | 17.9 | 18.9 | 20.0 | 21.0 |
| | 13-14' | 14.8 | 15.8 | 16.8 | 17.9 | 18.9 | 20.0 | 21.0 |
| | 14'-14 | 14.5 | 15.4 | 16.3 | 17.3 | 18.2 | 19.2 | 20.1 |

TABLE 2

Device Configuration for each length permutation.

| | | Graft No. | | | | | | |
|---|---|---|---|---|---|---|---|---|
| | Stent | T28 | T30 | T32 | T34 | T36 | T38 | T40 |
| | | | | Quantity of Stents | | | | |
| Graft Length = 120 mm | 11 | 1 | 1 | 1 | 1 | 1 | 1 | 1 |
| | 11' | 1 | 1 | 1 | 1 | 1 | 1 | 1 |
| | 12 | 1 | 1 | 1 | 1 | 1 | 1 | 1 |
| | 12' | 1 | 1 | 1 | 1 | 1 | 1 | 1 |
| | 13 + 14' | 5 | 5 | 4 | 4 | 4 | 3 | 3 |
| | 14 | 1 | 1 | 1 | 1 | 1 | 1 | 1 |
| Graft Length = 170 mm | 11 | 1 | 1 | 1 | 1 | 1 | 1 | 1 |
| | 11' | 1 | 1 | 1 | 1 | 1 | 1 | 1 |
| | 12 | 1 | 1 | 1 | 1 | 1 | 1 | 1 |
| | 12' | 2 | 2 | 2 | 2 | 2 | 2 | 2 |
| | 13 + 14' | 8 | 7 | 6 | 6 | 5 | 5 | 4 |
| | 14 | 1 | 1 | 1 | 1 | 1 | 1 | 1 |
| Graft Length = 220 mm | 11 | 1 | 1 | 1 | 1 | 1 | 1 | 1 |
| | 11' | 1 | 1 | 1 | 1 | 1 | 1 | 1 |
| | 12 | 1 | 1 | 1 | 1 | 1 | 1 | 1 |
| | 12' | 4 | 3 | 3 | 3 | 3 | 3 | 3 |
| | 13 + 14' | 9 | 9 | 8 | 8 | 7 | 6 | 6 |
| | 14 | 1 | 1 | 1 | 1 | 1 | 1 | 1 |

In the embodiment illustrated in FIG. 4, a hook 17 is shown attached to the outer surface of the sleeve 20. Hook 17 has two upper barbs 18 and two lower barbs 19 which protrude outwardly following deployment of the stent graft 10 for engagement with the inner luminal wall of the body vessel into which the stent graft 10 is to be deployed. Optionally, two hooks 17 are attached to each side of the stent graft 10, diametrically opposed to each other. The inclusion of hook 17 is optional.

Also shown in the embodiment illustrated in FIG. 4 is a stabilising strut 22 which bridges between stents 11 and 11' in order to stabilise the ring structure at this location to improve the sealing between the stent graft and the body wall of the vessel into which the stent graft is deployed. The inclusion of strut 22 is optional.

FIG. 5 shows an alternative embodiment of the stent graft prosthesis 10 of the present invention. The stent graft 10 comprises a tubular sleeve 20 of substantially constant cross section. Optionally, however, the tubular sleeve 20 may have a taper, such that the cross section of sleeve 20 varies along its length. As illustrated, the first stent element is formed from two ring stents 11,11'. Ring stents 11,11' are each formed from multiple windings of a resilient material such as PEEK or nitinol wire. Ring stent 11 adopts a shallow saddle shape (ie. with an oversize % of up to 3.5%) and is located on the terminal end of sleeve 20. Stent 11' can be circular or have a very shallow saddle shape, typically having a saddle height of up to 3.5 mm.

The second stent element is formed from four separate stents 12, 12' each formed from a continuous loop of multiple windings of a resilient stranded material such as PEEK or nitinol and each attached to the outer surface of the tubular sleeve 20 in a saddle shape. As illustrated, the second stent element has two distinct saddle shaped forms: stent 12 has a small saddle height relative to stent 12' with a larger saddle height. The comments as given above for the device of FIG. 4 in relation to the saddle height and number of stents present in second stent element 12,12' also apply to this embodiment.

As illustrated, the third stent element comprises six separate stents 13A-F each formed from a continuous loop of multiple windings of a resilient material such as PEEK or nitinol wire. Each stent 13A-F is formed into a saddle shape, with the saddle height remaining constant. The distance between each of the stents forming the third stent element, (ie. 13A-B, 13B-C etc.) can range from 14 mm to 22 mm depending upon the diameter of the fabric sleeve (generally the distance between the stents will increase with sleeve diameter). The saddle heights and number of stents 13 present on the graft can be varied as described above for FIG. 4. The stent graft prosthesis of FIG. 5 also includes a fourth stent element having two stents, 14' and 14. Stent 14' has a saddle shape similar to neighbouring stent 13, and is located so that its valleys 14A are adjacent (or within 2 mm of) the terminal stent 14. Stent 14 is of a circular configuration and has an inner diameter substantially identical to the outer diameter of sleeve 20. Together stents 14', 14 form a stable sealing zone for the graft terminus.

FIG. 6 shows the stent graft prosthesis illustrated in FIG. 5 with the strength of each stent set out in the aligned graph.

The invention claimed is:
1. An implantable prosthesis comprising:
i) a compliant and substantially fluid impervious tubular sleeve having a proximal end and a distal end with a conduit therethrough;

ii) a first stent element comprising at least one stent formed from multiple windings of wire fabricated from shape memory material, attached to said sleeve at a first location thereon;

iii) a second stent element attached to said sleeve comprising at least two separate stents, each formed from multiple windings of wire fabricated from shape memory material, each separate stent having a saddle shape configuration with two diametrically opposed peaks and two diametrically opposed valleys, the valleys being axially displaced relative to the peaks, wherein the peaks of each separate stent are aligned longitudinally; and iv) a third stent element attached to said sleeve configured to extend through an outwardly dilated portion of a vessel to treat the dilated portion when the prosthesis is positioned within the vessel comprising at least two separate stents, each formed from multiple windings of wire fabricated from shape memory material, each separate stent having a saddle shape configuration with two diametrically opposed peaks and two diametrically opposed valleys, the valleys being axially displaced relative to the peaks, wherein the peaks of each separate stent are aligned longitudinally and wherein the spacing of each stent of the third stent element is such that the peak of one stent is transversely aligned with the valley of each immediately neighboring stent of the third stent element, wherein each peak of each separate stent of the second stent element is longitudinally aligned with a peak of each separate stent of the third stent element, wherein the axial displacement between the peaks and valleys of each separate stent of the third stent element is larger than the axial displacement between the peaks and valleys of each separate stent of the second stent element, wherein the ring stents of each of the first stent element, the second stent element and the third stent element are not directly coupled to each other, and wherein at least one stent of at least one of the first stent element, the second stent element or the third stent element is positioned externally of the tubular graft.

2. The prosthesis as claimed in claim 1, wherein at least one stent of at least one of the first stent element, the second stent element or the third stent element is positioned internally of the tubular graft.

3. The prosthesis as claimed in claim 1, wherein the axial displacement between the peaks and valleys of each separate stent of the third stent element is greater than or equal to the spacing from that stent of the third stent element to each immediately neighboring stent.

4. A method of treating an aneurysm of the aortic arch, said method comprising inserting a prosthesis as claimed in claim 1 such that the first stent element sealingly engages with the inner luminal wall of the aorta, the second stent element provides the flexibility able to accommodate the angulation associated with the descending thoracic arch, and the third stent element provides axial and torsional stiffness required to ensure the integrity of the graft within the aneurysm sac and/or within the longer straighter section of the descending aorta.

5. An implantable prosthesis comprising:

i) a compliant and substantially fluid impervious tubular sleeve having a proximal end and a distal end with a conduit therethrough;

ii) a first stent element comprising at least one stent formed from multiple windings of wire fabricated from shape memory material, attached to said sleeve at a first location thereon;

iii) a second stent element attached to said sleeve comprising at least two separate stents, each formed from multiple windings of wire fabricated from shape memory material, each separate stent having a saddle shape configuration with two diametrically opposed peaks and two diametrically opposed valleys, the valleys being axially displaced relative to the peaks, wherein the peaks of each separate stent are aligned longitudinally; and iv) a third stent element attached to said sleeve comprising at least two separate stents, each formed from multiple windings of wire fabricated from shape memory material, each separate stent having a saddle shape configuration with two diametrically opposed peaks and two diametrically opposed valleys, the valleys being axially displaced relative to the peaks, wherein the peaks of each separate stent are aligned longitudinally, wherein each peak of each separate stent of the second stent element is longitudinally aligned with a peak of each separate stent of the third stent element, wherein the axial displacement between the peaks and valleys of each separate stent of the third stent element is larger than the axial displacement between the peaks and valleys of each separate stent of the second stent element, wherein the ring stents of each of the first stent element, the second stent element and the third stent element are not directly coupled to each other, wherein the saddle height of a stent of the third stent element is greater than or equal to the spacing from that stent of the third stent element to each immediately neighboring stent.

6. The prosthesis as claimed in claim 5, wherein the saddle height of a stent of the third stent element is from 10-25 mm.

7. The prosthesis as claimed in claim 5, wherein the saddle height of a stent of the third stent element is from 13-22 mm.

8. The prosthesis as claimed in claim 5, wherein the saddle height of each stent of the third stent element increases successively from one stent of the third stent element to the next with distance away from the second stent element.

9. The prosthesis as claimed in claim 5, wherein a distance D between two neighboring stents of the third stent element is from 0.5 cm to 5 cm.

10. The prosthesis as claimed in claim 5, wherein the third stent element comprises at least four independent ring stents each having an oversize of 20 to 30%.

11. The prosthesis as claimed in claim 10, wherein said third stent element comprises 5 to 10 independent ring stents each having an oversize of 20 to 30%.

12. The prosthesis as claimed in claim 10, wherein each independent stent of the third stent element has a saddle shape configuration with two diametrically opposed peaks and two diametrically opposed valleys, and wherein each independent stent of the third stent element is attached to the graft so that the peaks and valleys are longitudinally aligned with the peaks and valleys of the other independent stents of the third stent element.

13. The prosthesis as claimed in claim 5, wherein the spacing of each stent of the third stent element is such that the peak of one stent is transversely aligned with the valley of each immediately neighboring stent of the third stent element.

14. The prosthesis as claimed in claim 13, wherein the third stent element is configured to be positioned at an outwardly dilated portion of a vessel when the prosthesis is implanted within the vessel to treat the dilated portion.

15. The prosthesis as claimed in claim 5, comprising a fourth stent element which comprises an independent circular ring stent, wherein said fourth stent element further comprises an independent saddle shaped ring stent located adjacent the independent circular ring stent and at a distance ranging from touching the independent circular ring stent to about 2 mm.

16. The prosthesis as claimed in claim 5, wherein the first stent element comprises at least one independent ring stent having an inner circumference substantially identical to the outer circumference of the sleeve, wherein the second stent element comprises at least two independent saddle shaped stents each having a saddle height, wherein the saddle height is at least 5 mm, and wherein the third stent element comprises at least two independent saddle shaped stents each having a saddle height, wherein the saddle height is at least 10 mm, and
  wherein the independent stents of the first, second and third stent elements are not directly coupled to each other.

17. A method of treating an aneurysm of the aortic arch, said method comprising inserting a prosthesis as claimed in claim 5 such that the first stent element sealingly engages with the inner luminal wall of the aorta, the second stent element provides the flexibility able to accommodate the angulation associated with the descending thoracic arch, and the third stent element provides axial and torsional stiffness required to ensure the integrity of the graft within the aneurysm sac and/or within the longer straighter section of the descending aorta.

18. An implantable prosthesis comprising:
  i) a compliant and substantially fluid impervious tubular sleeve having a proximal end and a distal end with a conduit therethrough;
  ii) a first stent element comprising at least one stent formed from multiple windings of wire fabricated from shape memory material, attached to said sleeve at a first location thereon;
  iii) a second stent element attached to said sleeve comprising at least two separate stents, each formed from multiple windings of wire fabricated from shape memory material, each separate stent having a saddle shape configuration with two diametrically opposed peaks and two diametrically opposed valleys, the valleys being axially displaced relative to the peaks, wherein the peaks of each separate stent are aligned longitudinally;
  iv) a third stent element attached to said sleeve comprising at least two separate stents, each formed from multiple windings of wire fabricated from shape memory material, each separate stent having a saddle shape configuration with two diametrically opposed peaks and two diametrically opposed valleys, the valleys being axially displaced relative to the peaks, wherein the peaks of each separate stent are aligned longitudinally; and
  (v) a fourth stent element which comprises an independent saddle shaped ring stent located adjacent a terminal independent circular ring stent and at a distance ranging from touching the independent circular ring stent to about 2 mm,
  wherein each peak of each separate stent of the second stent element is longitudinally aligned with a peak of each separate stent of the third stent element,
  wherein the axial displacement between the peaks and valleys of each separate stent of the third stent element is larger than the axial displacement between the peaks and valleys of each separate stent of the second stent element,
  wherein the ring stents of each of the first stent element, the second stent element and the third stent element are not directly coupled to each other,
  wherein the saddle height of a stent of the third stent element is greater than or equal to the spacing from that stent of the third stent element to each immediately neighboring stent.

19. The prosthesis as claimed in claim 18, wherein the saddle height of a stent of the third stent element is from 10-25 mm.

20. The prosthesis as claimed in claim 18, wherein the saddle height of a stent of the third stent element is from 13-22 mm.

21. The prosthesis as claimed in claim 18, wherein the saddle height of each stent of the third stent element increases successively from one stent of the third stent element to the next with distance away from the second stent element.

22. The prosthesis as claimed in claim 18, wherein the spacing of each stent of the third stent element is such that the peak of one stent is transversely aligned with the valley of each immediately neighboring of the third stent element.

23. The prosthesis as claimed in claim 22, wherein the first and second stent elements are configured to sealingly engage with an inner luminal wall of a vessel, the second stent element is configured to extend within an angulating portion of the vessel, and the third stent is configured to extend within a portion of the vessel wherein the inner luminal wall is outwardly dilated, when then the prosthesis is positioned within the vessel to treat the dilated portion.

24. The prosthesis as claimed in claim 18, wherein the third stent element comprises at least four independent ring stents each having an oversize of 20 to 30%.

25. The prosthesis as claimed in claim 24, wherein said third stent element comprises 5 to 10 independent ring stents each having an oversize of 20 to 30%.

26. The prosthesis as claimed in claim 24, wherein each independent stent of the third stent element has a saddle shape configuration with two diametrically opposed peaks and two diametrically opposed valleys, and wherein each independent stent of the third stent element is attached to the graft so that the peaks and valleys are longitudinally aligned with the peaks and valleys of the other independent stents of the third stent element.

27. The prosthesis as claimed in claim 18, wherein the first stent element comprises at least one independent ring stent having an inner circumference substantially identical to the outer circumference of the sleeve, wherein the second stent element comprises at least two independent saddle shaped stents each having a saddle height, wherein the saddle height is at least 5 mm, and wherein the third stent element comprises at least two independent saddle shaped stents each having a saddle height, wherein the saddle height is at least 10 mm, and wherein the independent stents of the first, second and third stent elements are not directly coupled to each other.

28. A method of treating an aneurysm of the aortic arch, said method comprising inserting a prosthesis as claimed in claim 18 such that the first stent element sealingly engages with the inner luminal wall of the aorta, the second stent element provides the flexibility able to accommodate the angulation associated with the descending thoracic arch, and the third stent element provides axial and torsional stiffness required to ensure the integrity of the graft within the aneurysm sac and/or within the longer straighter section of the descending aorta.

* * * * *